US00PP29876P3

(12) United States Plant Patent
Olesen

(10) Patent No.: US PP29,876 P3
(45) Date of Patent: Nov. 27, 2018

(54) MINIATURE ROSE PLANT NAMED 'POULPAH077'

(50) Latin Name: ***Rosa* hybrid**
Varietal Denomination: Poulpah077

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 51 days.

(21) Appl. No.: 15/330,294

(22) Filed: Sep. 6, 2016

(65) Prior Publication Data

US 2018/0070492 P1 Mar. 8, 2018

(51) Int. Cl.
*A01H 5/02* (2018.01)
*A01H 6/74* (2018.01)

(52) U.S. Cl.
USPC ..... Plt./121
CPC ..... *A01H 5/02* (2013.01); *A01H 6/749* (2018.05)

(58) Field of Classification Search
USPC ..... Plt./116, 121
See application file for complete search history.

(56) References Cited

PUBLICATIONS

Perfection by Poulsen, Oct. 2013.*

* cited by examiner

*Primary Examiner* — Keith O. Robinson

(57) ABSTRACT

A new garden rose plant of the Miniature class which has abundant, coral pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulpah077'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2009 and the resulting seeds were planted in a controlled environment in Fredensborg, Denmark. The new variety, named 'Poulpah077', originated as a single seedling from the stated cross.

The new variety may be distinguished from its male pollen parent and female seed parent primarily by the following characteristics. The male pollen parent plant has orange red flowers while the new variety has coral pink flowers. The female seed parent plant is very compact, growing to 20 cm in one season, while the new variety is less compact, growing to 40 cm in one season.

The objective of the hybridization of this rose variety was to create a new and distinct variety for garden use with unique qualities, such as:

1. Uniform and abundant coral pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah077' from all other varieties of which we are aware.

As part of the rose development program, Mogens N. Olesen germinated the seeds from the aforementioned hybridization during winter of 2009 and conducted evaluations on the resulting seedlings in a controlled environment in Fredensborg, Denmark. 'Poulpah077' was selected in the spring of 2010 by the inventor as a single plant from the progeny of the aforementioned hybridization.

Asexual reproduction of 'Poulpah077' by traditional budding and rooted cuttings was first done by Mogens N. Olesen in the nursery in Fredensborg, Denmark in July, 2010. This initial and other subsequent asexual propagations conducted in controlled environments have demonstrated that the characteristics of 'Poulpah077' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah077'.

Specifically illustrated in FIG. 1 of the drawings are open flowers, petals detached, leaves, stems, sepals detached, and reproductive flower parts.

Figure 1:
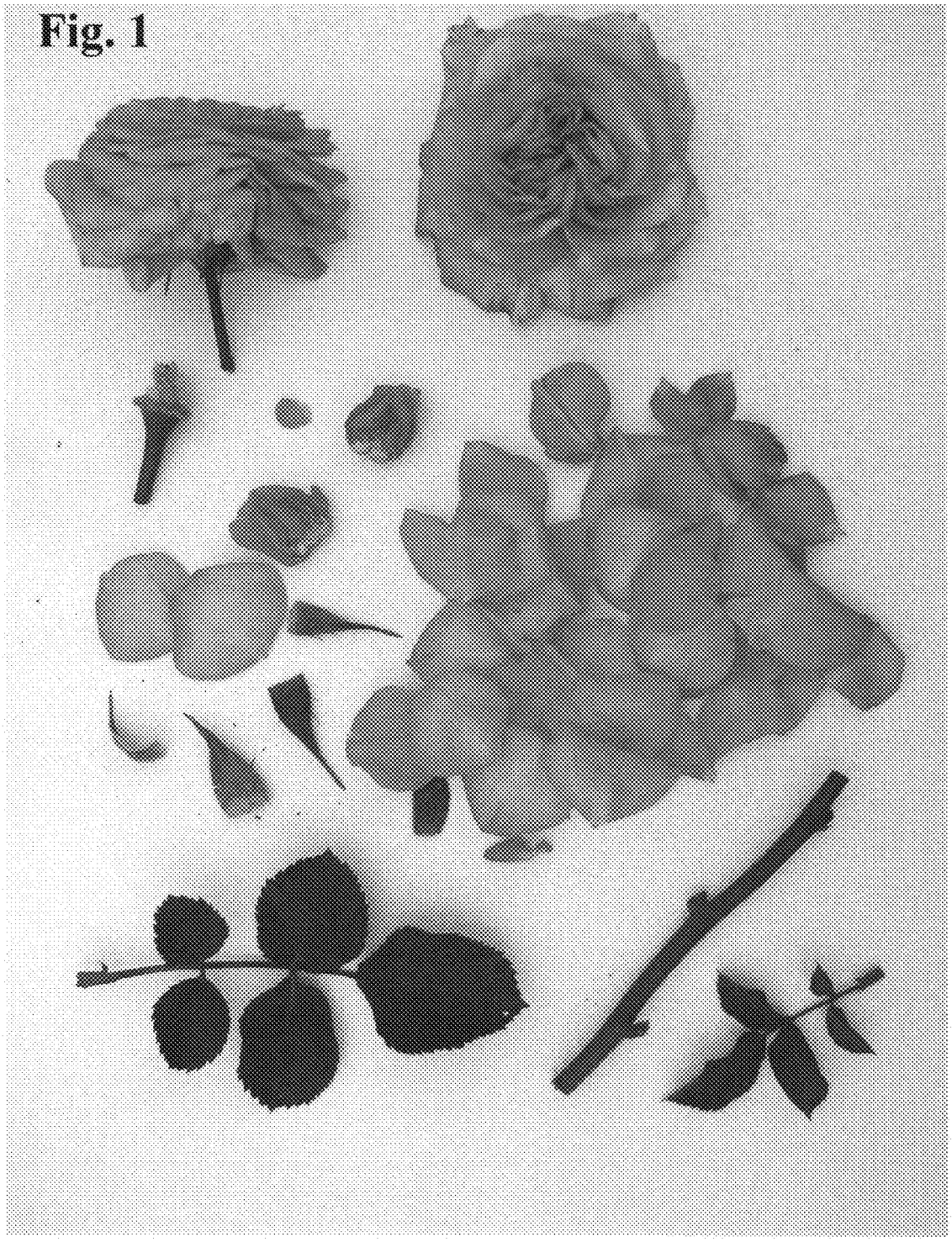
Figure 2:
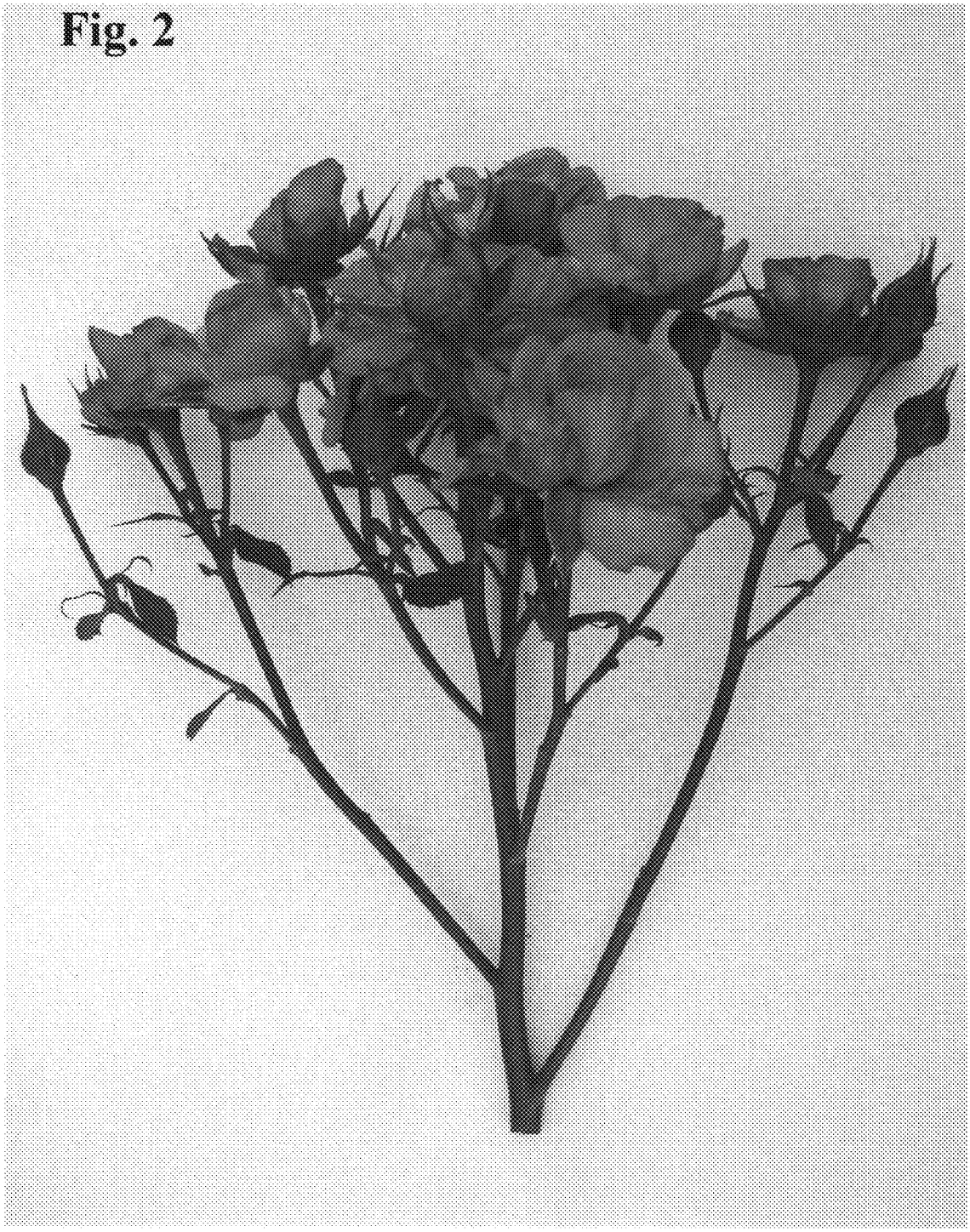

Illustrated in FIG. 2 is a flowering branch, showing attachment and arrangement of peduncles and quantity of flowers on a branch. Plants shown are 2 years of age.

DETAILED DESCRIPTION OF THE VARIETY

The following is a description of 'Poulpah077', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah033', U.S. Plant Pat. No. 17,509 are compared to 'Poulpah077' in Chart 1.

CHART 1

| | 'Poulpah077' | 'Poulpah033' |
|---|---|---|
| Petal Count | About 100 | 35 to 40 |
| Flower Diameter | 75 mm | 60 to 80 mm |
| General Tonality of Flower Color | Red Group 50B | Red-Purple Group N57A |

FLOWER AND FLOWER BUD

Blooming habit: Continuous.

Flower bud:

*Size*.—Upon opening, 20 mm in length from base of receptacle to end of bud. Bud diameter is 15 mm.

*Bud form*.—Ucerolate.

*Bud color*.—As sepals divide petals are Red Group 40A with intonations of Orange-Red Group N34A.

*Sepal inner surface*.—Color: Yellow-Green Group 145C with intonations of Greyed-Purple Group 183D. Surface: Lightly pubescent.

*Sepal outer surface*.—Color: Yellow-Green Group 144A with intonations of Greyed-Purple Group 183C. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—28 mm long, 10 mm wide.

*Receptacle*.—Texture: Smooth. Size: 8 mm in height, 13 mm wide. Color: Yellow-Green Group 144A with strong intonations of Greyed-Purple Group 183A. Shape: Campanulate.

*Pedicel*.—Surface: Smooth. Length: 25 to 30 mm. Diameter: 3 mm on average. Color: Greyed-Red Group 181A. Strength: Strong.

*Peduncle*.—Length: About 13 to 3 cm. Diameter: About 5 mm. Color: Yellow-Green Group 144A with intonations of Greyed-Red Group 180A. Texture: Smooth.

Flower bud development: Flower buds are borne in clusters of 5 flower buds on each peduncle, in panicle form.

Flower bloom:

*Fragrance*.—None.

*Duration*.—The blooms have a duration on the plant of approximately 7 to 10 days. Petals fall cleanly away from plant after flowers have fully matured.

*Size*.—Flower diameter is 75 mm when open. Flower depth is 40 mm.

*Flower shape*.—Quartered-rosette, very double, with many overlapping petals packed into quarter sections.

Petalage: Under normal conditions, flowers have about 100 petals total.

General tonality of flower: Open flowers are Red Group 50B.

Petal color:

*Upon opening, outer petals*.—Upper surface: Red Group 48C. Lower surface: Mainly Red Group 55C. Margins are Red Group 52C.

*Upon opening, inner petals*.—Upper surface: Red Group 48C. N. Lower surface: Mainly Red Group 55C. Margins are Red Group 52C.

*Basal petal spots, upon opening*.—Upper surface: Yellow Group 10A. Lower surface: Yellow Group 10C.

*After opening*.—Upper surface: Red Group 48C. Lower surface: Mainly Red Group 55C. Margins are Red Group 52C.

*After opening, inner petals*.—Upper surface: Red Group 48C. Lower surface: Mainly Red Group 55C. Margins are Red Group 52C.

*Basal petal spots, after opening*.—Upper surface: Yellow Group 10A. Lower surface: Yellow Group 10C.

Petals:

*Petal reflex*.—Somewhat reflexed.

*Margin*.—Entire and uniform.

*Shape*.—Generally rounded. Apex shape: Rounded. Base shape: Acute.

*Size*.—35 mm (l)×40 mm (w).

*Texture*.—Smooth.

*Thickness*.—Average.

Petaloids:

*Size*.—15 mm (l) by 10 mm (w).

*Quantity*.—About 15.

*Shape*.—Irregular, asymmetric, with a rounded apex and acute base.

*Color*.—Upper surface is Red Group 48C. The lower surface is Red Group 55C. Basal petaloid spots, are Yellow Group 10A on the upper surface, and Yellow Group 10C on the lower surface.

Reproductive flower parts:

*Pollen*.—None observed.

*Anthers*.—Size: 2 mm in length. Color: Yellow-Orange Group 22A. Quantity: 30 on average.

*Filaments*.—Color: White Group 155A. Length: 6 mm.

*Pistils*.—Length: 10 mm. Quantity: 20 on average.

*Stigmas*.—Color: Yellow-Green Group 145D.

*Styles*.—Color: Yellow-Green Group 145D.

*Location of stigmas*.—Superior in location relative to the length of the filaments and the height of the anthers.

*Hips*.—None Observed.

PLANT

Plant growth: Upright, bushy. Plants are 40 cm in height, and 40 cm wide.

Stems:

*Color*.—Juvenile growth: Yellow-Green Group 144A with intonations of Greyed-Purple Group 185 A. Mature growth: Yellow-Green Group 144A with intonations of Greyed-Purple Group 185A .

*Length*.—On average, canes are 20 cm from the base of the plant to the flowering portion.

*Diameter*.—7 mm.

*Internodes*.—On mature canes about 30 mm between nodes.

*Surface texture*.—Young wood: Smooth. Older wood: Smooth.

Long prickles:

*Incidence*.—None observed.

Plant foliage:

*Compound leaf.*—120 mm (l)×75 (w).

*Quantity.*—3 leaves per 10 cm of stem on average.

*Leaf bearing angle to the stem.*—45 degrees.

*Color of juvenile foliage.*—Upper side: Yellow-Green Group 144A. Lower side: Yellow-Green Group 144B.

*Color of mature foliage.*—Upper side: Yellow-Green Group 147A. Lower side: Yellow-Green Group 146B.

Plant leaves and leaflets:

*Stipules.*—Size: 6 mm long, 2 mm wide. Quantity: 2 per compound leaf. Shape: Linear, slightly broad based with outward extending apices. Margins: Finely serrated. Color: Yellow-Green Group 144A.

*Petiole.*—Length: 30 mm. Diameter: 2 mm.

*Upper surface.*—Color: Yellow-Green Group 144A with intonations of Greyed-Red Group 181A.

*Lower surface.*—Color: Yellow-Green Group 144A.

*Rachis.*—Length: 40 mm. Upper surface: Color: Yellow-Green Group 144A with intonations of Greyed-Red Group 181A.

*Lower surface.*—Color: Yellow-Green Group 144A.

*Leaflet.*—Quantity: Normally 5 leaflets. Margins: Serrated. Size: On average terminal leaflets are 50 mm long, 35 mm wide. Shape: Generally elliptical. Base: Rounded. Apex: Cuspidate. Texture: Smooth. Thickness: Average. Arrangement: Odd pinnate. Venation: Reticulate. Glossiness: Moderate.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah077', substantially as illustrated and described herein, due to its abundant coral pink flowers, disease resistance, and extended period of bloom.

* * * * *